United States Patent
Michelsson et al.

(10) Patent No.: US 7,973,931 B2
(45) Date of Patent: Jul. 5, 2011

(54) METHOD FOR DETERMINING THE POSITION OF THE EDGE BEAD REMOVAL LINE OF A DISK-LIKE OBJECT

(75) Inventors: Detlef Michelsson, Wetzlar-Naunheim (DE); Guido Dietzler, Rabenau (DE)

(73) Assignee: Vistec Semiconductor Systems GmbH, Weilburg (DE)

( * ) Notice: Subject to any disclaimer, the term of this patent is extended or adjusted under 35 U.S.C. 154(b) by 429 days.

(21) Appl. No.: 12/231,465

(22) Filed: Sep. 3, 2008

(65) Prior Publication Data

US 2009/0130784 A1 May 21, 2009

(30) Foreign Application Priority Data

Sep. 6, 2007 (DE) .......................... 10 2007 042 271

(51) Int. Cl.
 *G01B 11/00* (2006.01)
 *G01B 11/14* (2006.01)
 *G06K 9/00* (2006.01)
(52) U.S. Cl. ......... 356/401; 356/614; 356/620; 382/151
(58) Field of Classification Search .................. None
See application file for complete search history.

(56) References Cited

U.S. PATENT DOCUMENTS

| | | | |
|---|---|---|---|
| 6,920,249 B2 | 7/2005 | Rinn et al. | 382/199 |
| 7,142,300 B2 | 11/2006 | Rosengau | 356/369 |
| 7,197,178 B2 | 3/2007 | Simpkins | 382/145 |
| 7,382,450 B2 | 6/2008 | Heiden | 356/237.1 |
| 7,616,804 B2 * | 11/2009 | Pai et al. | 382/145 |
| 2003/0030050 A1 | 2/2003 | Choi | 257/4 |
| 2005/0122509 A1 | 6/2005 | Backhauss | 356/237.2 |
| 2005/0280807 A1 | 12/2005 | Backhauss et al. | 356/237.2 |
| 2006/0286811 A1 | 12/2006 | Heiden et al. | 438/759 |
| 2007/0076194 A1 | 4/2007 | Michelsson | 356/237.1 |

FOREIGN PATENT DOCUMENTS

| | | |
|---|---|---|
| DE | 102 32 781 | 2/2004 |
| DE | 10 2004 029 012 | 1/2006 |
| DE | 10 2005 014 594 | 10/2006 |
| DE | 10 2005 018 743 | 10/2006 |
| DE | 10 2005 028 427 | 1/2007 |

OTHER PUBLICATIONS

Ingrid Peterson et al.: "Lithography Defects: Reducing and Managing Yield Killers through Photo Cell Monitoring", Spring 2000, Yield Management Solutions.

* cited by examiner

*Primary Examiner* — Tari Chowdhury
*Assistant Examiner* — Gordon J Stock, Jr.
(74) *Attorney, Agent, or Firm* — Davidson, Davidson & Kappel, LLC (57) ABSTRACT

A method for determining the position of an edge bead removal line of a disk-like object having an edge area and an alignment mark on the edge area is disclosed, wherein the edge area including the edge bead removal line is imaged on a line-by-line basis, an intensity profile I of the imaged edge area including the edge bead removal line is obtained with a camera on a line-by-line basis, and the edge area and the alignment mark are detected, wherein the local intensity maxima $I'_{max}$ of the intensity profile I are plotted as points in a diagram, segment sets are formed in the diagram, the segment sets are fitted in ellipses, and a quality criterion $q_{ges}$ is determined for each ellipse.

18 Claims, 6 Drawing Sheets

METHOD FOR DETERMINING THE POSITION OF THE EDGE BEAD REMOVAL LINE OF A DISK-LIKE OBJECT

This claims the benefit of German Application No. DE 10 2007 042 271.9, filed on Sep. 6, 2007 and hereby incorporated by reference herein.

The present invention relates to a method for determining the position of an edge bead removal line of a disk-like object. In particular, the present invention relates to a method for determining the position of the edge bead removal line of a disk-like object having an edge area and an alignment mark on the edge area, wherein the edge area including the edge bead removal line is imaged, an intensity profile of the imaged edge area including the edge bead removal line is determined by a camera on a line-by-line basis and the edge area and the alignment mark are detected, wherein the local intensity maxima of the intensity profile are plotted as points on a diagram, segment sets are formed in the diagram, the segment sets are fitted into ellipses, and for each ellipse a quality criterion is determined.

BACKGROUND

Methods, arrangements and apparatus for determining the position of the edge bead removal line of an object, for example a wafer, are well known from the practice. Herein, the postures and locations, in other words "positions", of structures are determined on the object.

In semiconductor manufacture, disk-like objects (wafers) are coated with photoresist during the manufacturing process. The photoresist is first subjected to an exposure and then to a development process. It is structured in these processes for subsequent process steps. Slightly more photoresist is deposited on the edge area of the wafer than in the center of the wafer due to manufacturing conditions. This is how an edge bead is produced. Photoresist on the edge of the wafer and the edge bead can lead to the contamination of manufacturing machines and to defects on the wafer in the subsequent processing steps.

To avoid these effects, an edge bead removal (EBR) is carried out. Defects in the width of the edge bead removal result from imprecise alignment of the corresponding edge bead removal apparatus relative to the wafer. Further sources of error can be the imprecise alignment of the illumination apparatus relative to the wafer during exposure of the photoresist. Herein, an edge bead removal which is too extensive, leads to a reduction of the usable wafer area and therefore to a loss of produced chips. An edge bead removal which is too small, can lead to a contamination of the subsequently applied resist layers or other structures in the edge area of the wafer. Since in both cases the productivity of the manufacturing process is reduced, the edge bead removal, as well as many other defects, is constantly monitored during the manufacturing process. Herein both the width of the edge bead removal and whether an edge bead removal has been carried out at all are checked.

For the purpose of orientation, wafers usually have a mark on the substrate edge, a so-called alignment mark. This alignment mark can be either a notch or a flat on the wafer edge. This alignment mark allows the wafer to be unequivocally oriented.

In order to determine the position of the edge bead removal line (EBR line) of the wafer, it is necessary to determine the position of the wafer edge. Herein, however, usually neither the position of the wafer on the rotary stage nor the position of the camera line is in correspondence with the centerpoint of the rotary stage. This is why the edge bead removal line is not in correspondence with the centerpoint of the rotary stage either, which makes determination of the position of the edge bead removal line of the wafer difficult. Due to the lack of correspondence between the edge bead removal line and the centerpoint of the rotary stage, there are often imprecisions and errors in determination of the position of the edge bead removal line.

Apparatuses are known for detecting various structures on the surface of the wafer by means of image detection. Herein, the wafer is illuminated in the bright-field mode and scanned by means of a camera (matrix or line camera).

Such an inspection machine by KLA-Tencor Corporation is described in the article entitled "Lithography Defects: Reducing and Managing Yield Killers through Photo Cell Monitoring" by Ingrid Peterson, Gay Thompson, Tony DiBiase and Scott Ashkenaz, Spring 2000, Yield Management Solutions. The wafer inspection machine described there relies on an incident-light illumination means for inspecting microdefects with low contrast in a bright-field illumination mode.

Laid-open German Patent Application DE 102 32 781.5 discloses an apparatus for wafer inspection for making the line caused by the edge bead removal determinable, so that it is distinguishable from other lines or edges to be determined on the wafer.

A method for removing and for improved detection of the edge bead is known, for example, from U.S. Pat. No. 7,142, 300 B2. In this document it is suggested that the contrast between the silicon layer of the wafer and the applied photoresist layer can be improved by using a specialized illumination. For this purpose, the wafer is to be illuminated separately with s- and p-polarized light in the vicinity of the Brewster angle of silicon or the photoresist layer. Subsequently, the difference between the images of the reflected s-polarized radiation and the image of the reflected p-polarized radiation is evaluated for contrast enhancement. The use of polarized light, however, requires additional optical components.

U.S. Pat. No. 7,197,178 B2 discloses a method for measuring the edge bead removal, which also includes the determination of a line or edge at the circumference of the wafer. The position of the wafer notch at the edge of the wafer and the position of the center of the wafer are determined. Also, the distance between the edge of the wafer and an edge bead removal line on the circumference of the wafer is determined. The edge bead removal line is then determined from a bright field and a dark field, the method is based, however, on a technical idea which is different from the present invention.

Laid-open German Patent Application DE 10 2005 014 594.9 discloses a method for detecting incomplete edge bead removal of a wafer, wherein first an edge area of a reference object is imaged. Marks are defined in the edge area of the reference object. Finally, images of edge areas of a plurality of objects of one lot are recorded. The inspection of the objects is exclusively limited to the positions of the marks defined on the reference object. The use of reference objects and a plurality of lots is, however, complex.

Laid open German Patent Application DE 10 2005 018 743.9 discloses a method for imaging the edge of a wafer with a suitable method, in particular, in a dark-field image on a suitable detector, such as a line camera. The lines or edges present on the wafer edge are detected, and then a decision process is carried out to identify an edge bead removal line.

German Patent DE 10 2005 028 427 discloses a method for optically imaging a wafer with a photoresist layer, wherein an imaging area on the surface of the wafer is illuminated with light and a fluorescence image is recorded of the imaging area on the basis of the fluorescent light emitted by the excited light due to the illumination. The evaluation method is very complex, however, when fluorescent light is used.

German Patent DE 10 2004 029 012 discloses a method for inspecting the edge bead removal of a wafer, wherein an optical image of the area to be inspected is recorded, wherein first a first optical image is recorded prior to the application of a layer on the wafer disk and then a second optical image is recorded after the at least partial removal of this layer, and then the imaged area of the wafer surface is inspected by comparing the first and the second image.

As already mentioned above, in the arrangements, apparatuses and methods from the prior art in the field of wafer inspection, the position of the edge bead removal line of a wafer is determined in a relatively complex way (comparison of reference images) or as an approximation. As the requirements with respect to precision become more stringent, it is increasingly doubtful that the position of the edge bead removal line can be determined with sufficient precision, which is why more general approaches are required.

SUMMARY OF THE INVENTION

It is an object of the present invention to provide a method allowing the size and position of the edge area created by edge bead removal, i.e. the size and position of the edge bead removal line, to be determined automatically, more precisely and more reliably in comparison with prior-art methods.

The present invention provides a method for determining the position of the edge bead removal line of a disk-like object, comprising the features of claim 1. Further advantages can be derived from the dependent claims and the description.

In the method according to the present invention for determining the position of the edge bead removal line, the disk-like object includes at least one edge area and an alignment mark. The method according to the present invention includes several steps which will be described in the following.

First, the edge area of the disk-like object is imaged line-by-line with a camera for wafer inspection from the prior art. Herein, the camera includes a detector line for sequentially generating a series of image lines. For recording the plurality of image lines, the wafer is rotated past the detector line. It is assumed that the edge area includes an edge bead removal line. With the aid of the camera, a line based intensity profile I of the imaged edge area with the edge bead removal line is determined. From the imaged intensity profile, the profile of the edge area and the position of the alignment mark are determined according to a well-known method from the prior art.

In one embodiment, the surface of the edge area of the disk-like object facing away from the camera is illuminated by a light source in a bright-field arrangement. The edge area to be imaged and facing the camera is illuminated with another light source in a dark-field arrangement. The edge line is then determined according to a well known approximation method from the prior art, wherein it is derived from the plurality of the intensity profiles imaged on a line-by-line basis. The edge line results from the distinct transition within the registered intensity profiles between the dark-field arrangement and the bright-field arrangement. This is how the object underside illumination results in an exact representation of the edge line of the object in the image. The intensity profile includes a marked deviation which describes the position of the alignment mark within the edge line.

After determination of the edge line which limits the outer edge area of the object, the position of the alignment mark is determined in the plurality of intensity profiles recorded on a line-by-line basis in a subsequent step again according to a well known approximation method from the state of the art. In one embodiment, the position of the alignment mark is determined by the zero positions of a second-order polynomial, wherein the parameter of this polynomial can be derived from the deviation values of the previously determined edge line.

The points of the edge line found irrespective of the alignment mark are now transformed into Cartesian coordinates and then fitted into an ellipsoid according to a further approximation method from the prior art, which describes the edge line. The ellipsoid is a circle in the ideal case, providing there is no displacement and/or rotation of the disk-like object and the object is a circular wafer. In one embodiment, the ellipsoid is determined for the edge line according to the least squares method, wherein a method by R. Halir and J. Flusser can be used, which will be described later. From the data of the ellipsoid for the edge line of the disk-like object, the displacement and/or the rotation of the disk-like object on the pre-aligner is determined according to a method from the prior art. The determination of the position of the edge line of the disk-like object is thus complete.

Next, in a plurality of steps, the position of the edge bead removal line on the disk-like object is determined, or it is decided whether the object has an edge bead removal line at all.

With a light source for a dark-field arrangement, a bright point within an individual image line imaged by the camera arises at each photoresist edge on the object, which results in a local maximum $I'_{max}$ in the intensity profile I of the image line. The next step is then to determine the position of such a point within the intensity profile I for the image line with high precision. Herein, it must be noted that the intensity profile I usually has more than one local maximum. This is due to the fact that other structures on the disk-like object also result in a similar image with a bright point, wherein the intensity maxima are smaller, however. Further details of an intensity profile I will be described with reference to the following figures.

According to the present invention, the local intensity maxima $I'_{max}$ of the intensity profiles I for the edge region of the object will be plotted as points in a two-dimensional diagram. The diagram thus takes all image lines into account recorded with the detector line of the camera for the edge region of the object, wherein a smaller number of image lines can also be reckoned with (data reduction). This diagram has an x axis on which the relative position of an individual point on the object within the associated image line is plotted. The diagram has a y axis on which the line number of each image line imaged with the camera is plotted for each point. Those (x; y) points are plotted in the diagram for which local intensity maxima $I'_{max}$ where found in the previous steps. The magnitude of the intensity is plotted in the diagram for point (x; y).

In the following, certain threshold values and limitations can be set for the preferred embodiments of the present invention, to facilitate the determination of the position of the edge bead removal line on the object.

Figure 6:
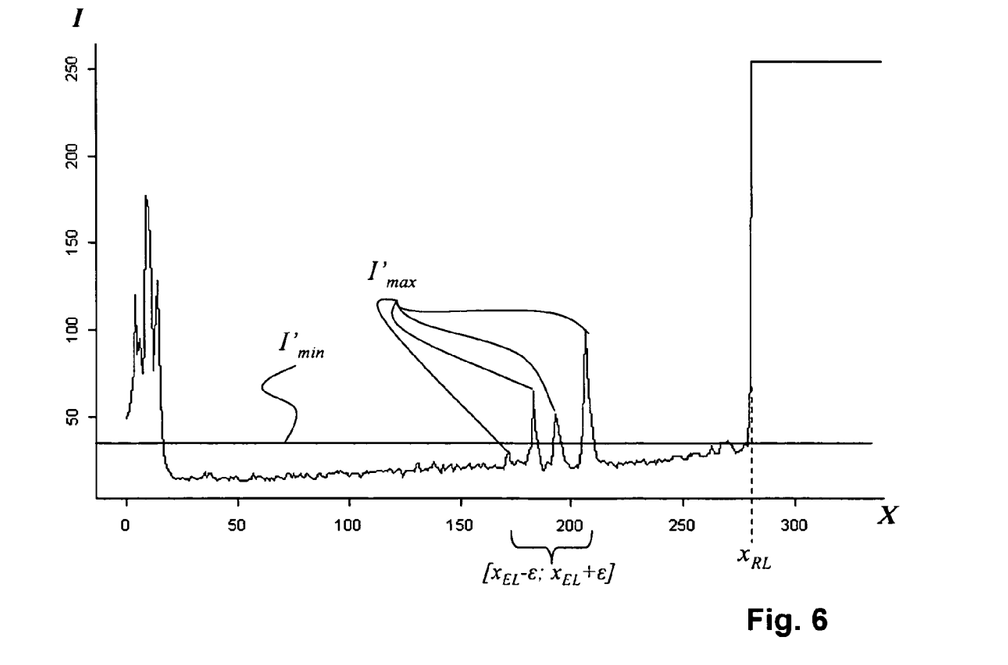
FIG. 6 is a diagram for an intensity profile of a typical image line recorded by a camera for wafer inspection.

First, according to one embodiment of the present invention, a threshold value $I'_{max}$ is determined, from which a local intensity maximum $I'_{max}$ is used for the diagram (cf. description with reference to FIG. 6). In a further embodiment, the individual positions (x; y) on the object are determined for each intensity maximum $I'_{max}$ by a polynomial, on which the intensity maxima $I'_{max}$ lie.

In some of the processing steps of the edge bead removal, almost all photoresist is removed, and only a very small photoresist residue remains on the disk-like object. This photoresist residue does not form continuous lines in the position of the EBR. Moreover, bright points also form on all other photoresist edges not belonging to the edge bead removal line. For determination of the edge bead removal line, however, only the ends—toward the edge line of the disk-like object—of these photoresist residues are to be used. Since one main reason for EBR, i.e. contamination with photoresist splashes, only occurs when the distance between the edge bead removal line and the edge line of the disk-like object is too small, this minimum distance can be determined. To determine the edge bead removal line and therefore to establish the diagram, at least the first local intensity maximum $I'_{max1}$ from the direction of the edge line of the disk-like object as determined in the previous steps, should always be used for each image line. The result of the evaluation is a series of intensity maxima $I'_{max1}$ for each image line, which are plotted in the diagram as described above.

In the next step of the method according to the present invention, segments are formed in the diagram described above, wherein each segment consists of a set of points (x; y) having similar intensity I and which are densely grouped about a predetermined x value. More precisely, this means that the intensities I of the points of an individual segment lie within a predetermined I interval and that moreover the x coordinates of the points of this one segment are within a predetermined x interval. Therefore, for one segment, all x values for the segment points (x; y) should lie within an interval $[X_{const1}-\epsilon_1; X_{const1}+\epsilon_1]$ to be determined about a fixed value $X_{const1}$ of the x axis of the diagram, because all points of the edge bead removal line to be determined are also usually in such a small x interval. All points (x; y) of an individual segment are thus densely grouped about a segment-dependent x value.

In the next step of the method according to the present invention, those segments are combined in a segment set having x values of the segment set points (x; y) within an interval $[X_{const2}-\epsilon_2; X_{const2}+\epsilon_2]$ about a fixed value $X_{const2}$ of the x axis of the diagram. In this way, all points (x; y) of an individual segment set are again densely grouped about a segment-set-dependent x value—as with the points (x; y) of a segment. The intensities I of the points (x; y) of a segment set need not lie, however, within an I interval unlike the points (x; y) of a segment. This is not necessary for determining the edge bead removal line, since the points (x; y) of the edge bead removal line can have varying intensities I.

Along the y axis there may be interruptions, i.e. it may be that segments or segment sets do not continuously extend along the entire y axis, since similar local intensity maxima $I'_{max}$ may not be found in each image line y, or no local intensity maxima $I'_{max}$ may be found at all. In the case of several closely spaced, segments in an image line $y_{const}$, i.e. within an interval about a fixed value $y_{const}$ to be set, in an embodiment of the present invention, only that segment which has the highest local intensity maximum $I'_{max}$ is used for determining the associated segment set, since higher intensities indicate an edge bead removal line with a higher probability than low intensities.

The segments remaining after the above described segment creation, are defined as one-segment sets, so that all segments now have a segment set to which they belong.

Short segment sets can arise from interfering structures on the disk-like object and are not taken into account in the further discussion, since the edge bead removal line to be determined in the following extends along almost the entire y axis, except for the area of the alignment mark. In one embodiment of the present invention, therefore only those segment sets are used for determining the position of the edge bead removal line which have a number of image lines y extending across the individual segment set, above a threshold value $y_{min}$ to be set for the number of image lines y.

In a similar fashion as for the determination of the edge line of the disk-like object by the formation of an ellipse, in the next step of the method according to the present invention, an ellipse is also sought for the edge bead removal line. To do this, however, a plurality of ellipses are first formed by fitting one ellipse in each of the remaining segment sets. In one embodiment of the present invention, the ellipses for the edge bead removal line are determined with the least squares method. To do this, according to a further embodiment, a method by R. Halir and J. Flusser is used which will be briefly described in the following. An implicit two-dimensional second-order polynomial is used:

$$F(x,y)=ax^2+bxy+cy^2+dx+ey+f=0 \tag{G1}$$

With the following limitation, this polynomial describes an ellipse:

$$b^2-4ac<0 \tag{G2}$$

(x; y) are points on the ellipse. The method according to R. Halir and J. Flusser determines parameters a, b, c, d, e, f in order to minimize the following term:

$$\min_{a,b,c,d,e,f} \sum_i F(x_i, y_{i'})^2 \tag{G3}$$

Auxiliary parameters $c_1, c_2, C_3$ are calculated:

$$c_1 = \frac{cd^2 - bde + ae^2}{4ac - b^2} - f \tag{G4}$$

$$c_2 = \frac{\sqrt{(a-c)^2 + b^2}}{2} \tag{G5}$$

$$c_3 = \frac{-1}{2ac - \frac{b^2}{2}} \tag{G6}$$

However, the radii of $r_{min}$ and $r_{max}$ (main axes) and the focus point having the positional coordinates $d_x$ and $d_y$ of the ellipse are needed, which can be calculated as follows:

$$r_{min} = \sqrt{\frac{c_1}{\frac{a+c}{2} + c_2}} \tag{G7}$$

$$r_{max} = \sqrt{\frac{c_1}{\frac{a+c}{2} - c_2}} \tag{G8}$$

$$d_x = c_3\left(cd - \frac{be}{2}\right) \tag{G9}$$

$$d_y = c_3\left(ae - \frac{bd}{2}\right) \tag{G10}$$

The decision as to which of the ellipses describes the edge bead removal line is taken in the following step of the method according to the present invention by means of a quality criterion $q_{ges}$ which also serves to decide whether or not there is an edge bead removal line at all. The quality criterion $q_{ges}$ is determined for each ellipse of the edge bead removal line. In one embodiment, the quality criterion $q_{ges}$ for an individual ellipse is determined as a product from the coverage $q_C$ of each ellipse by segment sets and the average intensity $q_I$ of all points (x; y) along each ellipse:

$$q_{ges} = q_C * q_I \tag{G11}$$

Thus, the longer the segment set associated with the ellipse extends along the y axis, the more points (x; y) are included by the segment set, and the brighter an ellipse is of the edge bead removal line, the greater the likelihood that this ellipse describes the edge bead removal line. The distance of the edge bead removal line to the edge line is then a quantity for the edge bead removal.

In another embodiment of the present invention, a threshold value $q_{gesmin}$ is determined for the quality criterion $q_{ges}$, above which an ellipse is only taken into account at all for determination of the edge bead removal line. If the $q_{ges}$ values for all ellipses are below the threshold value $q_{gesmin}$ it can be assumed that there is no edge bead removal line on the object. The measured values of the edge bead removal can then be compared with the production specifications of the semiconductor manufacturer. If there are deviations, the production processes can be adapted accordingly in order to ensure optimal yield in the manufacturing process.

In the following, the two factors $q_C$, $q_I$ of the quality criterion $q_{ges}$ are defined more precisely according to the above described embodiment. The following applies for the coverage factor $q_C$:

$$q_C = \frac{N_s}{N_{ges}} \tag{G12}$$

wherein $N_s$ is the number of points from segment sets of each ellipse in question. $N_{ges}$ is the number of image lines overall. Therefore, $N_s \leq N_{ges}$ always applies. However, due to the alignment mark, an ellipse can never be covered up to 100%, which means that $q_C$ is usually really smaller than 1.0. To eliminate the effect of the alignment mark—only the edge area of the disk-like object without the alignment mark is relevant for a discussion of the coverage by segment sets—in a preferred embodiment, threshold values are determined which generally lead to the not covered areas of the edge region, such as that of the alignment mark, being ignored. For this purpose, a lower threshold value $C_{min}$ is determined, below which the coverage factor $q_C$ is given the value 0.0. Accordingly, an upper threshold value $C_{max}$ is determined, from which the coverage factor $q_C$ is given the value 1.0. Additionally, a normalization is carried out for the coverage factor $q_C$ to the interval [0.0, 1.0]. In combination, for the coverage factor $q_C$ the following results from equation G12:

$$q_C = \begin{cases} \text{Term} = \dfrac{\frac{N_s}{N_{ges}} - C_{min}}{C_{max} - C_{min}} & \text{if Term} < 1.0 \\ 0.0 & \text{if Term} < 0.0 \\ 1.0 & \text{else} \end{cases} \tag{G13}$$

In one embodiment, for example, $C_{min}=10\%$ and $C_{max}=80\%$ is determined.

The following results for the intensity factor $q_I$:

$$q_I = \frac{\sum_{i=0}^{N_s} p_i}{N_s} \tag{G14}$$

wherein $p_i$ are the intensity values of the points (x; y) of each ellipse in question. In accordance with the above described reasoning for the threshold values of the coverage factor $q_C$, a maximum intensity cannot be reached for the intensity factor $q_I$ either. Since no light impinges on the detector (detector line) of the camera in the area of the alignment mark the integrated intensity over the entire circumference of the object is therefore smaller than the integrated intensity of an object without alignment mark over the same area. Therefore, in a preferred embodiment, a lower threshold value $I_{min}$ is determined, below which the intensity factor $q_I$ is given the value 0.0. Additionally, an upper threshold value $I_{max}$ is determined, from which the intensity factor $q_I$ is given the value 1.0. The threshold values $I_{min}$, $I_{max}$ lead to only the relevant intensity values I being taken into account. Additionally, a normalization for the intensity factor $q_I$ is carried out to the interval [0.0, 1.0]. In combination, from equation G14, this results in the following:

$$q_I = \begin{cases} \text{Term} = \dfrac{\frac{\sum_{i=0}^{N_s} p_i}{N_s} - I_{min}}{100 * (I_{max} - I_{min})} & \text{if Term} < 1.0 \\ 0.0 & \text{if Term} < 0.0 \\ 1.0 & \text{else} \end{cases} \tag{G15}$$

In one embodiment, for example, $I_{min}=20$ and $I_{max}=80$ is determined.

The ellipse in the area of the edge bead removal line having the highest quality criterion $q_{ges}$ therefore describes the edge bead removal line with the highest probability and the solution is found. Thus, all the steps of the method according to the present invention have been described.

Since the method is primarily used for wafer inspection, the disk-like object in this case is a wafer which has a plurality of structures formed on its surface.

BRIEF DESCRIPTION OF THE DRAWINGS

The method according to the present invention will be described in more detail with reference to the schematic drawings, wherein.

DETAILED DESCRIPTION

Figure 1:
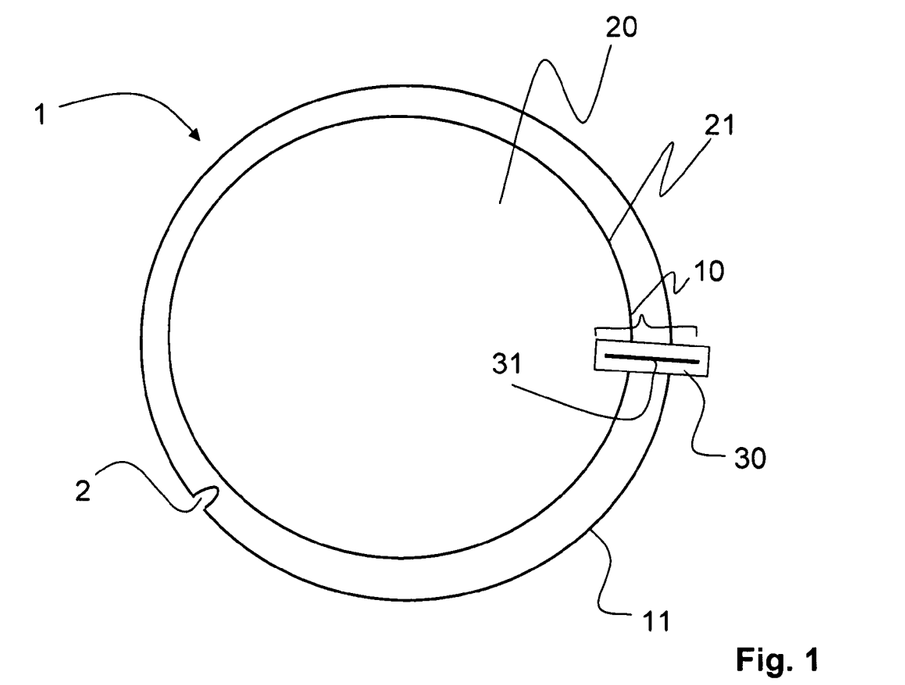
FIG. 1 is a schematic top view of a measuring arrangement for detecting the edge bead removal line of an object.

FIG. 1 is a schematic top view of a measuring arrangement for detecting the edge bead removal line 21 of an object 1. Object 1, in the present view, is a wafer having an edge area 10 with an edge line 11 at its furthest end. Edge area 10 rotates below an inspection device, for example a camera 30. Edge area 10 is imaged on an imaging detector of camera 30, wherein imaging on a line-by-line basis, one detector line 31 after another, of the wafer is carried out. The imaging method can be, for example, basically those methods known from the field of microscopy, such as bright-field, dark-field or special contrast methods (cf. FIG. 5). However, a preferred method is one which particularly highlights edge bead removal line 21 to be detected on object 1. This can be achieved, for example, by using dark-field imaging. A layer of photoresist 20 is provided on object 1, which does not reach to edge line 11 of object 1 and therefore has an edge bead removal line 21. Photoresist layer 20 rotates together with edge bead removal line 21 below camera 30 with the detector of camera 30. An alignment mark 2 is arranged on edge area 10 of object 1 which can reach across edge bead removal line 21 into the area of object 1, on which photoresist layer 20 is applied.

Figure 2:
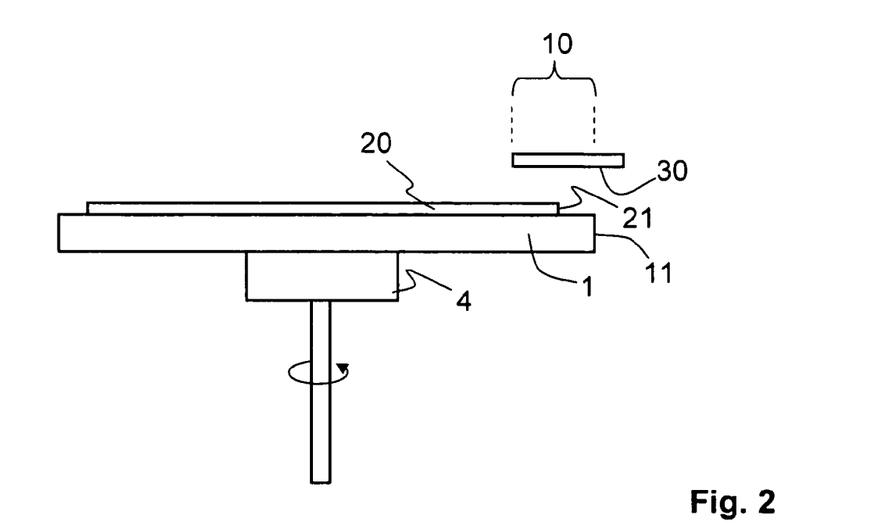
FIG. 2 is a schematic perspective view of a measuring arrangement for detecting the edge bead removal line of an object.

FIG. 2 is a schematic perspective view of the measuring arrangement for detecting edge bead removal line 21 of an object 1 according to FIG. 1. Object 1, in this case the wafer, is supported on a rotatable measuring stage 4. Photoresist layer 20 is not applied across the entire width of object 1, since an edge bead removal has been carried out at edge area 10. The length of edge area 10 is indicated by two broken lines and a curly bracket at the top of the drawing. Edge area 10 includes at least edge line 11, edge bead removal line 21 and the partial area of edge area 10 which has its photoresist removed and is limited by edge line 11 and edge bead removal line 21. Camera 30 moves over edge area 10 of object 1 and records images on a line-by-line basis, from which intensity profiles are obtained on edge area 10.

Figure 3:
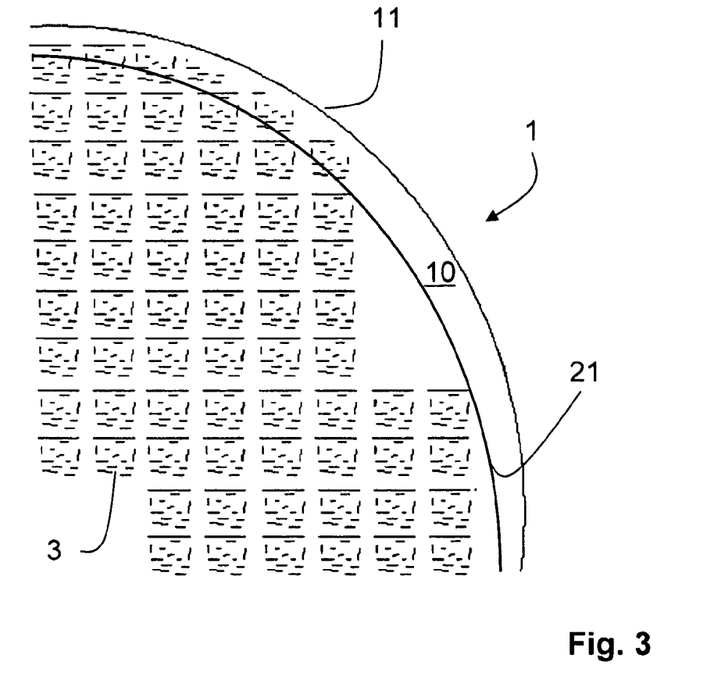
FIG. 3 is a schematic view of a section of an edge area, wherein structures arranged in dies are on the object.

FIG. 3 is a schematic view of a section of edge area 10 of object 1, which again, is a wafer in the embodiment shown. On object 1, there are structures arranged in dies 3. In the top left partial area of edge area 10, edge bead removal has not been completely carried out, since some portions of dies 3 reach into edge area 10. The intensity profiles for this partial area of edge area 10 have local intensity maxima in dark-field illumination, which arise from the structures of dies 3 on edge area 10. Dies 3 can therefore be "interfering structures" in determining the position of edge bead removal line 21.

Figure 4:
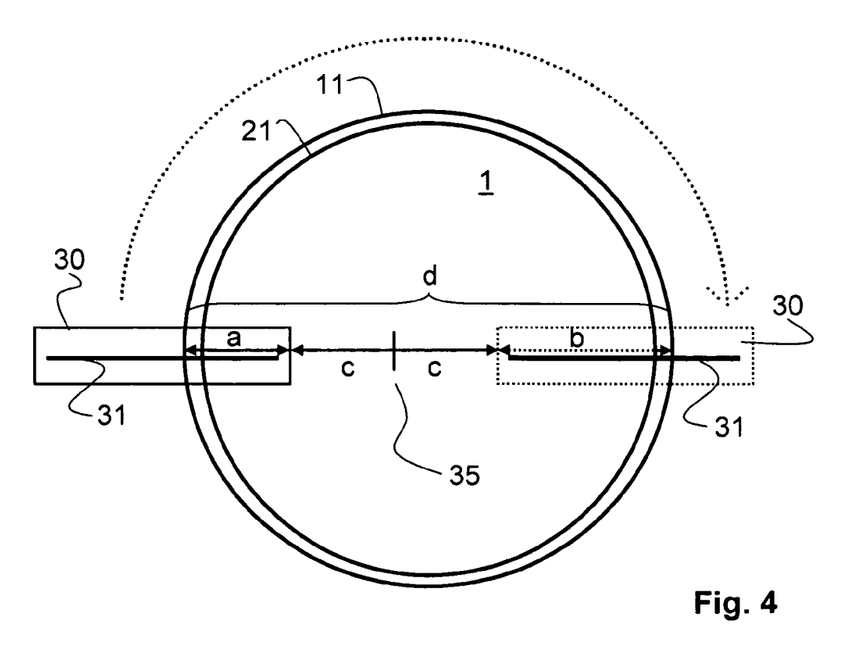
FIG. 4 is a schematic view for determining the position of a camera for wafer inspection on the entire wafer area.

FIG. 4 is a schematic view for determining the position of a camera 30 for inspecting a disk-like object 1, which again is a wafer, across the entire surface of object 1. To determine the position of the edge bead removal on object 1, it is necessary to determine the position of edge area 10 of object 1, wherein edge area 10 includes edge line 11 and edge bead removal line 21. Camera 30 is a line camera, which is a CCD chip in a particular embodiment. Camera 30 records the intensities of the partial area of object 1 present below the measuring window (not shown) of camera 30. Herein, neither the position of object 1 on measuring stage 4, nor the position of camera 30 is in relation to the centerpoint of measuring stage 4. FIG. 4 shows how the position of camera 30 can be determined.

There is a relative movement between camera 30 and edge area 10. In the example shown, camera 30 assumes a first position in which a is the relative distance of edge line 11 within the associated image line $31_n$ at rotary angle α (rotary angle α is not shown) (shown by camera 30 with an uninterrupted line). It is advantageous if the wafer rotates below camera 30 to record the next image. Herein, the wafer moves (shown with a dotted direction arrow) so that camera 30 passes further across edge area 10 until it reaches a second position. In the second position of camera 30, b is the relative distance of edge line 11 within the associated image line $31_n$ at a rotary angle α+180° (shown by camera 30 with a dotted line).

The camera position is defined by prealigner center 35, which is spaced from camera 30 with a length c to be determined in all positions of camera 30 across edge area 10. The relative distances a and b and diameter d of object 1 are known. Then using the following equation, distance c of camera 30 to prealigner center 35 can be determined:

$$c = \frac{d-a-b}{2} \quad (G16)$$

Figure 5:
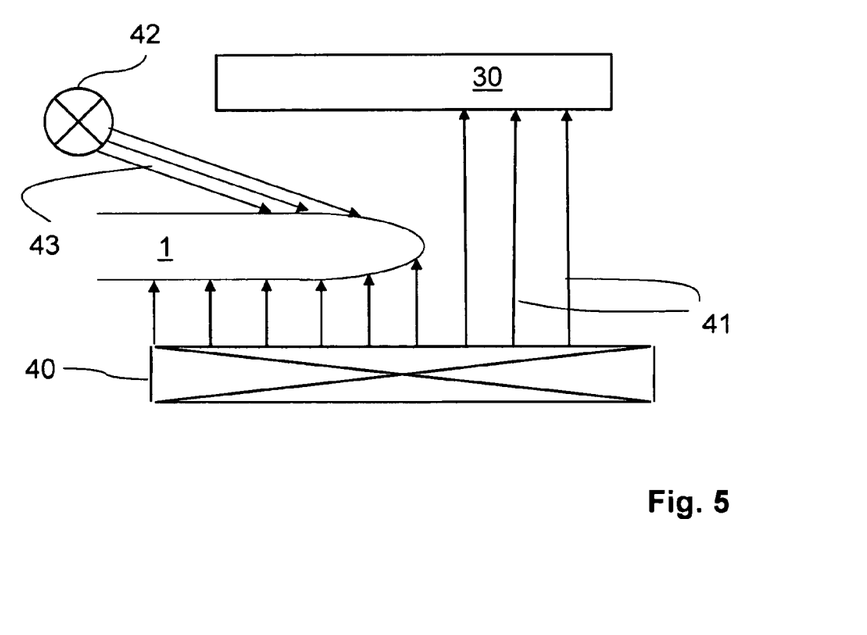
FIG. 5 is a schematic side view of an arrangement of an object, a camera for wafer inspection and the illumination emitted by two light sources for determining the position of an edge area of the object.

FIG. 5 is a schematic side view of an arrangement of an object 1, a camera 30 for wavelength inspection and an illumination emitted by two light sources 40, 42 for the determination of the position of edge area 10 of object 1. The lower surface of edge area 10 faces away from camera 30 and is illuminated by light source 40 in a bright-field arrangement according to the prior art through beam path 41. Edge area 10 facing camera 30 and to be imaged by camera 30 is illuminated by incident-light light source 42 in a dark-field arrangement via beam path 43 obliquely from the top according to the prior art. Incident-light light source 42, from a vertical point of view is below camera 30 and above object 1. A dark-field view of the edge line of the photoresist of photoresist layers having the edge bead removed can be achieved, for example, by having the incident-light light source 42 directed from the central area of object 1 toward edge area 10, and thus not passed directly into the detector of camera 30.

FIG. 6 is a diagram of an intensity profile of a typical and exemplary image line $31_n$ which represents the image of a line on the surface of edge area 10 of object 1 generated by camera 30 (one-dimensional). The relative position of an individual point within image line $31_n$ is plotted along the x axis. The intensity I of the points of image line $31_n$ is plotted along the y axis.

The almost vertical line at $x_{RL} \approx 280$ shows the distinct changeover from the dark-field illumination to the bright-field illumination. The intensity profile shown here for image line $31_n$ therefore includes a coordinate $x_{RL}$ belonging to an (x; y) point 12 on edge area 10, which is taken into account according to the present invention in the determination of the position of edge line 11. All points (x; y) from image line $31_n$ with $x > x_{RL} + \epsilon$ are not on object 1. All points (x; y) on image line $31_n$ with $x < x_{RL} - \epsilon$ are on object 1.

During the process of edge bead removal, almost all photoresist is removed. Only a very small residue remains. This residue does not form continuous lines in the position of the EBR. Moreover, bright points also arise at all other photoresist edges, so that the intensity profile of an image line $31_n$ usually has a plurality of local intensity maxima $I'_{max}$. For determining the position of edge bead removal line 21, however, only the end of these photoresist residues are to be used on object 1. Moreover, it should be noted that the intensities measured for photoresist residues on edge bead removal line 21 only occur from a certain intensity range upward, so that a threshold value $I'_{min}$ can be determined, from which local intensity maxima $I'_{max}$ are taken into account in the method according to the present invention. Four local intensity maxima $I'_{max}$ are shown left of the x position found for edge line 11, wherein the first and lowest local intensity maximum $I'_{max}$ is below the threshold value $I'_{min}$ and is therefore not taken into account in the further discussion, and the other three, higher, local intensity maxima $I'_{max}$ are above the threshold value $I'_{min}$ and are therefore taken into account in the further discussion. In the following steps of the method according to the present invention it is determined which of the three remaining local intensity maxima $I'_{max}$ is part of edge bead removal line 21 and whether or not it belongs to edge bead removal line 21.

In the area around x≈10, there are structures on object 1 which also give rise to local intensity maxima $I'_{max}$, which are, however, too far away from the possible area of object 1 which is relevant for determining the position of edge bead removal line 21.

Figure 7:
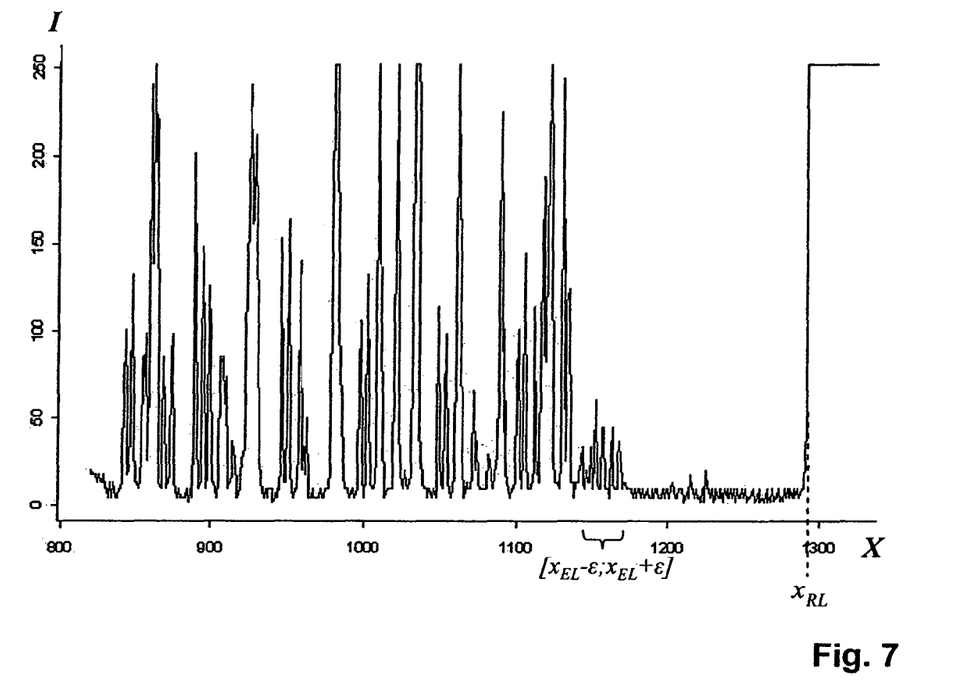
FIG. 7 is a diagram of an intensity profile with small amounts of photoresist on the object.

FIG. 7 is a diagram of an intensity profile for an image line $31_n$ with little photoresist on object 1, wherein the same coordinate system is used as in FIG. 6. The x position of edge line 11 is in the area around x≈1300, the x position for edge bead removal line 21 is in the area around x≈1150.

Figure 8:
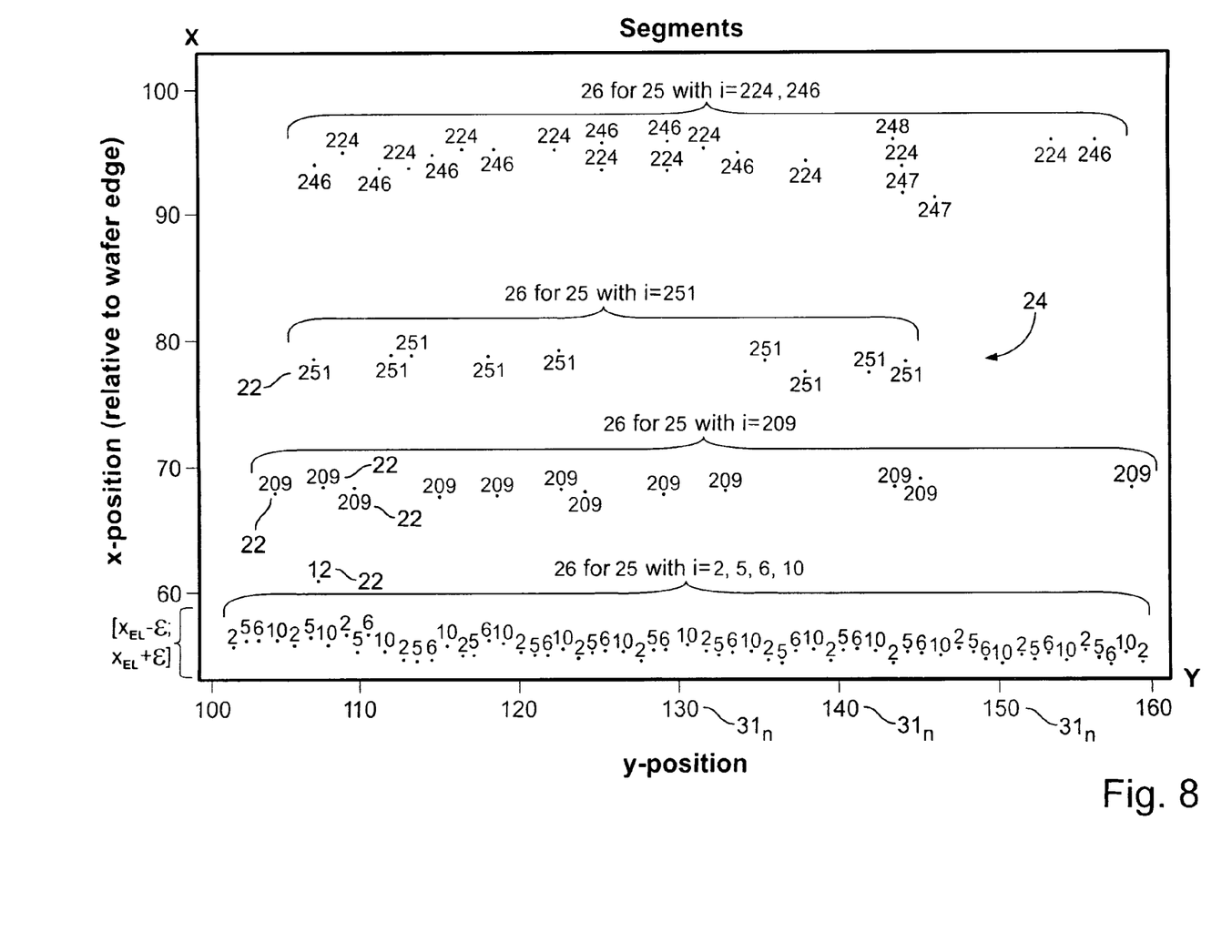
FIG. 8 is a diagram showing the formation of a plurality of segments and segment sets on the object.

FIG. 8 is a diagram 24 showing the formation of a plurality of segments 25 and segment sets 26 on object 1.

In each of FIGS. 6, 7 intensity profile I is shown for a single image line 31. For each recorded image line $31_n$ those local intensity maxima $I'_{max}$ are determined which should be inspected for the next step in the method according to the present invention. For each image line $31_n$ exactly one x area for edge line 11 and another x area for edge bead removal line 21 can always be determined. The result of the above evaluation is a series of local intensity maxima $I'_{max}$ for each image line $31_n$. To determine edge bead removal line 21, however, the entire edge area 10, that is the plurality of image lines $31_n$ in question, has to be inspected. This is why the local intensity maxima $I'_{max}$ found and taken into account according to the method according to the present invention are concatenated across all image lines $31_n$ in the next step of the method according to the present invention, to produce at least one segment 25. To do this, all inspected image lines $31_n$ are taken into account in a diagram 24. On the x axis of diagram 24, as in FIGS. 6, 7, the relative positions of an individual point 22 are plotted within the associated image line $31_n$. Unlike FIGS. 6, 7, the line numbers of each of the image lines $31_n$ imaged with detector line 31 of camera 30 are shown along the y axis. Then the remaining local intensity maxima $I'_{max}$ are entered as points 22 in diagram 24. Next to each point 22, index i (segment index) is entered for the associated segment 25, which was formed according to the inventive method.

From the example shown in FIG. 8 it can be derived that points 22 belonging to four segments 25 having indices i=2, 5, 6, 10 are almost continuously present in the area around x=60 along the y axis, wherein the individual segments 25 having indices i=2, 5, 6, 10, seen individually, do not extend along the entire y axis. In the area around x=70, a segment 25 having the index i=209 is formed, in the area around x=80 a segment 25 having an index i=251, and in the area around x=100 a segment 25 having an index i=225 and i=246 is formed, respectively. The four segments 25 with i=209, 251, 224, 246, seen individually, do not continuously extend along the entire y axis, either.

In the next step of the method according to the present invention, those segments 25 are combined to a segment set 26, which lie within an interval about a fixed value $X_{const}$ of the x axis of diagram 24. In the example shown, the four segments 25 having indices i=2, 5, 6, 10 about x=60 are combined in a segment set 26, segments 25 having indices i=224, 226 about x=100 are combined to a further segment set 26. Segment 25 having an index i=209 about x=70 and segment 25 having an index i=251 about x=80 each form a one-element segment set 26.

If, as described above, a threshold value $y_{min}$=20 is determined for the number of image lines $31_n$, across which each segment set 26 is to extend to be taken into account in determining the position of edge bead removal line 21, the two segment sets 26 having segment indices i=209 and i=251, are omitted, since they extend over less than 20 image lines $31_n$. The two segment sets 26 having segment indices i=2, 5, 6, 10 and i=224, 226, are left over.

According to the inventive method, as described above, an ellipse 23 is fitted into each of the two remaining segment sets 26, and the quality criterion $q_{ges}$ is calculated for each of them. In the example according to FIG. 8, ellipse 23 for segment set 26 having segment indices i=2, 5, 6, 10 has a higher coverage of points 22 and therefore a higher coverage factor $q_C$ as compared to segment sets 26 having segment indices i=224, 246. A decision with respect to the two intensity factors $q_I$ of the two ellipses 23 can therefore not be reached from diagram 24, since no data with respect to the intensities can be derived from diagram 24. A determination of edge bead removal line 21 is therefore not obvious from diagram 24 in the present example, but can only be made by means of calculating the quality criterion $q_{ges}$ for each of the two ellipses 23 while taking the intensity factors $q_I$ still to be calculated into account.

Figure 9:
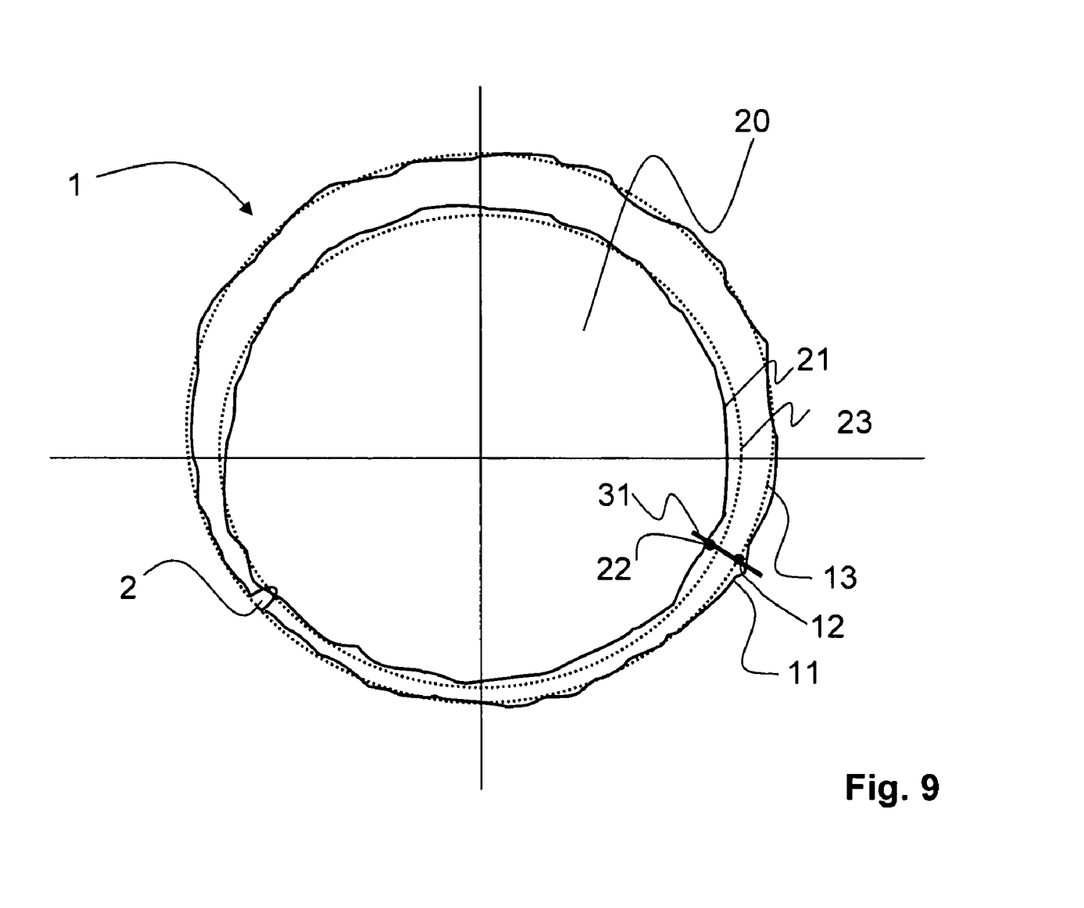
FIG. 9 is a schematic top view of a wafer with an ellipse for each of the approximated representations of the edge line and the edge bead removal line.

FIG. 9 is a schematic top view of an object 1, again, a wafer. According to the inventive method, an ellipse 13 (dotted line) has been determined for edge line 11 (solid line) and an ellipse 23 (dotted line) has been determined for edge bead removal line 21 (solid line), which are shown here in a Cartesian coordinate system so that the ellipsoid forms can be seen in FIG. 9—unlike the representation in FIG. 8, wherein ellipses 13, 23 are shown as point sets or segment sets 26 along an imaginary straight line. The representation in FIG. 9 is exaggerated in order to make deviations from the real edge line 11 with respect to ellipse 13, or deviations of the real edge bead removal line 21 with respect to ellipse 23, more visible.

Finally, it should be noted in particular, that the above discussed exemplary embodiments only serve to describe the claimed teachings, they should not be construed, however, as limiting the latter to the exemplary embodiments. In particular, the camera does not necessarily need to be a line camera, other cameras according to the prior art can also be used, allowing an intensity profile to be recorded for the edge area of object 1 in a systematic way, and with which the further steps of the method according to the present invention can be carried out (formation of segments 25, segment sets 26, determination of quality criterion $q_{ges}$).

What is claimed is:

1. A method for determining a position of an edge bead removal line of a disk-like object having an edge area and an alignment mark on the edge area, comprising the following steps:
    imaging the edge area on a line-by-line basis, where it is assumed that said edge area comprises at least the edge bead removal line, wherein a detector line of a camera is used to determine an intensity profile I on a line-by-line basis of the imaged edge area comprising the edge bead removal line;
detecting the edge area;
detecting the alignment mark;
plotting a local intensity maxima $I'_{max}$ of the intensity profile I as points in a diagram having an x axis, on which a relative position of an individual point imaged with the detector line of the camera is plotted within an associated image line of the detector line, and having a y axis, on which a line number of the associate image line is plotted for each point;
forming segments in the diagram, wherein each segment comprises a set of points, and intensities of the points of the segments are within a predetermined interval, wherein the x coordinates of the set of points of each segment are within a predetermined other interval;
combining at least some of the segments into at least one segment set wherein the x coordinates of the points of the segments for the respective segment set are within an interval, and wherein segments remaining after the combining of the at least some of the segments form one-element segment sets;
fitting each segment set into one respective ellipse; and
determining a quality criterion $q_{ges}$ for each ellipse, so as to determine whether or not each ellipse in question belongs to the edge bead removal line.

2. The method according to claim 1, wherein that a surface of the edge area of the disk-like object which faces away from the camera is illuminated by a light source in a bright-field arrangement.

3. The method according to claim 1, wherein a threshold value $I'_{min}$ is determined, above which a local intensity maximum $I'_{max}$ is used for the diagram.

4. The method according to claim 1, wherein per image line imaged by the detector line of the camera, at least a first local intensity maximum $I'_{max1}$ from a direction of an edge line is used for creating the diagram.

5. The method according to claim 1, wherein in the case of a plurality of adjacent segments lying within an interval about a fixed value $y_{const}$ of the y axis of the diagram on an image line imaged by the detector line of the camera, wherein the segment having a highest local intensity maximum $I'_{max}$ is used for determining an associated segment set.

6. The method according to claim 1, wherein segment sets are taken into account for determining the position of the edge bead removal line, which have a number of image lines across which an individual segment set extends which is above a threshold value $y_{min}$ for the number of image lines.

7. The method according to claim 1, wherein ellipses for the edge bead removal line are determined with a least square method.

8. The method according to claim 1, wherein for each ellipse for the edge bead removal line, the quality criterion $q_{ges}$ is determined as the product from a coverage $q_C$ of a respective ellipse by segment sets and an average intensity $q_I$ of all points along the respective ellipse.

9. The method according to claim 1, wherein the disk-like object is a wafer, having a plurality of structures formed on its surface.

10. The method according to claim 1, wherein ellipses are taken into account for determining the position of the edge bead removal line, for which the quality criterion $q_{ges}$ is above a threshold value a $q_{gesmin}$.

11. The method according to claim 1, wherein an edge area facing the camera and to be imaged by the camera is illuminated by a light source in a dark-field arrangement.

12. The method according to claim 8, wherein for a determination of coverage factors $q_C$, a lower threshold value $C_{min}$ is determined, below which an individual coverage factor $q_C$ is given a minimum value, and in that an upper threshold value $C_{max}$ is determined, above which an individual coverage factor $q_C$ is given a maximum value.

13. The method according to claim 8, wherein for a determination of intensity factors $q_I$ a lower threshold value $I_{min}$ is determined, below which an individual intensity factor $q_I$ is given a minimum value, and in that an upper threshold value $I_{max}$, is determined, above which an individual intensity factor $q_I$ is given a maximum value.

14. The method according to claim 11, wherein an edge line is determined from a plurality of the intensity profiles imaged on a line-by-line basis, wherein the edge line results from a changeover between the dark-field arrangement and a bright-field arrangement, which is obtained from the intensity profiles detected by the camera.

15. The method according to claim 14, wherein the position of the alignment mark in the plurality of the intensity profiles imaged on a line-by-line basis is determined from zero positions of a second order polynomial, wherein parameters of the second order polynomial are derived from deviation values from the edge line.

16. The method according to claim 15, wherein the points of the edge line, not including points forming the alignment mark, are transformed into Cartesian coordinates and fitted into an ellipse for the edge line.

17. The method according to claim 16, wherein the ellipse for the edge line is determined according to a least square method.

18. The method according to claim 16, wherein a displacement and/or a rotation of the disk-like object on a prealigner is determined from data of the ellipse for the edge line of the disk-like object.

* * * * *

UNITED STATES PATENT AND TRADEMARK OFFICE
CERTIFICATE OF CORRECTION

PATENT NO. : 7,973,931 B2
APPLICATION NO. : 12/231465
DATED : July 5, 2011
INVENTOR(S) : Detlef Michelsson and Guido Dietzler It is certified that error appears in the above-identified patent and that said Letters Patent is hereby corrected as shown below:

Claim 2 in Column 13, line 28, should read:

--The method according to claim 1, wherein a surface...-- instead of

"The method according to claim 1, wherein that a surface..."

Claim 5 in Column 13, line 41, should read:

--a fixed value $y_{const}$ of the $y$ axis of the diagram on an image line...-- instead of

"a fixed value $y_{const}$ of they axis of the diagram on an image line..."

Claim 10 in Column 14, line 12, should read:

--a threshold value $q_{gesmin}$...-- instead of

"a threshold value a $q_{gesmin}$..."

Signed and Sealed this
Twenty-fifth Day of October, 2011

David J. Kappos
*Director of the United States Patent and Trademark Office*